US008597673B2

(12) United States Patent
Trollsas et al.

(10) Patent No.: US 8,597,673 B2
(45) Date of Patent: Dec. 3, 2013

(54) COATING OF FAST ABSORPTION OR DISSOLUTION

(75) Inventors: Mikael O. Trollsas, San Jose, CA (US); Michael Huy Ngo, San Jose, CA (US); Bozena Zofia Maslanka, Aptos, CA (US); Syed Faiyaz Ahmed Hossainy, Fremont, CA (US); Lothar W. Kleiner, Los Altos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 636 days.

(21) Appl. No.: 11/638,780

(22) Filed: Dec. 13, 2006

(65) Prior Publication Data

US 2008/0145393 A1 Jun. 19, 2008

(51) Int. Cl.
*A61F 2/82* (2013.01)
*A61P 9/10* (2006.01)

(52) U.S. Cl.
USPC .......................................... 424/423; 523/113

(58) Field of Classification Search
None
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,170,043 A | 10/1979 | Knight et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |

(Continued)

FOREIGN PATENT DOCUMENTS

DE 42 24 401 1/1994
EP 0 301 856 2/1989

(Continued)

OTHER PUBLICATIONS

Nakabayashi et al. Bio-Medical Materials and Engineering 14, 345-354 (2004).*
Iwasaki et al. in Colloids and Surfaces B; Biointerfaces 32 (2003) 77-84.*
Invitation to Pay Additional Fees for PCT/US2007/087151, mailed Feb. 19, 2009, 6 pgs.
U.S. Appl. No. 10/807,362, Glauser.
Anonymous, *Cardiologists Draw-Up the Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cqi/document?req=1061847871753, printed Aug. 25, 2003 (2 pages).

(Continued)

*Primary Examiner* — Dennis Heyer
(74) *Attorney, Agent, or Firm* — Squire Sanders (US) LLP

(57) ABSTRACT

A coating of fast absorption or fast dissolution on an implantable device and methods of making and using of the coating are provided.

8 Claims, 2 Drawing Sheets

(56) References Cited

U.S. PATENT DOCUMENTS

| | | | |
|---|---|---|---|
| 5,759,205 A | 6/1998 | Valentini | |
| 5,776,184 A | 7/1998 | Tuch | |
| 5,783,657 A | 7/1998 | Pavlin et al. | |
| 5,788,979 A | 8/1998 | Alt et al. | |
| 5,800,392 A | 9/1998 | Racchini | |
| 5,820,917 A | 10/1998 | Tuch | |
| 5,824,048 A * | 10/1998 | Tuch | 128/898 |
| 5,824,049 A | 10/1998 | Ragheb et al. | |
| 5,830,178 A | 11/1998 | Jones et al. | |
| 5,837,008 A | 11/1998 | Berg et al. | |
| 5,837,313 A | 11/1998 | Ding et al. | |
| 5,849,859 A | 12/1998 | Acemoglu | |
| 5,851,508 A | 12/1998 | Greff et al. | |
| 5,854,376 A | 12/1998 | Higashi | |
| 5,857,998 A | 1/1999 | Barry | |
| 5,858,746 A | 1/1999 | Hubbell et al. | |
| 5,865,814 A | 2/1999 | Tuch | |
| 5,869,127 A | 2/1999 | Zhong | |
| 5,873,904 A | 2/1999 | Ragheb et al. | |
| 5,876,433 A | 3/1999 | Lunn | |
| 5,877,224 A | 3/1999 | Brocchini et al. | |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | |
| 5,932,299 A | 8/1999 | Katoot | |
| 5,955,509 A | 9/1999 | Webber et al. | |
| 5,958,385 A | 9/1999 | Tondeur et al. | |
| 5,962,138 A | 10/1999 | Kolluri et al. | |
| 5,971,954 A | 10/1999 | Conway et al. | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,011,125 A | 1/2000 | Lohmeijer et al. | |
| 6,015,541 A | 1/2000 | Greff et al. | |
| 6,033,582 A | 3/2000 | Lee et al. | |
| 6,034,204 A | 3/2000 | Mohr et al. | |
| 6,042,875 A | 3/2000 | Ding et al. | |
| 6,051,576 A | 4/2000 | Ashton et al. | |
| 6,051,648 A | 4/2000 | Rhee et al. | |
| 6,054,553 A | 4/2000 | Groth et al. | |
| 6,056,993 A | 5/2000 | Leidner et al. | |
| 6,060,451 A | 5/2000 | DiMaio et al. | |
| 6,060,518 A | 5/2000 | Kabanov et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,110,483 A | 8/2000 | Whitbourne et al. | |
| 6,113,629 A | 9/2000 | Ken | |
| 6,120,491 A | 9/2000 | Kohn et al. | |
| 6,120,536 A | 9/2000 | Ding et al. | |
| 6,120,788 A | 9/2000 | Barrows | |
| 6,120,904 A | 9/2000 | Hostettler et al. | |
| 6,121,027 A | 9/2000 | Clapper et al. | |
| 6,129,761 A | 10/2000 | Hubbell | |
| 6,136,333 A | 10/2000 | Cohn et al. | |
| 6,143,354 A | 11/2000 | Koulik et al. | |
| 6,153,252 A | 11/2000 | Hossainy et al. | |
| 6,159,978 A | 12/2000 | Myers et al. | |
| 6,165,212 A | 12/2000 | Dereume et al. | |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | |
| 6,211,249 B1 | 4/2001 | Cohn et al. | |
| 6,214,901 B1 | 4/2001 | Chudzik et al. | |
| 6,231,600 B1 | 5/2001 | Zhong | |
| 6,240,616 B1 | 6/2001 | Yan | |
| 6,245,753 B1 | 6/2001 | Byun et al. | |
| 6,245,760 B1 | 6/2001 | He et al. | |
| 6,248,129 B1 | 6/2001 | Froix | |
| 6,251,136 B1 | 6/2001 | Guruwaiya et al. | |
| 6,254,632 B1 | 7/2001 | Wu et al. | |
| 6,258,121 B1 | 7/2001 | Yang et al. | |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,299,604 B1 | 10/2001 | Ragheb et al. | |
| 6,306,176 B1 | 10/2001 | Whitbourne | |
| 6,331,313 B1 | 12/2001 | Wong et al. | |
| 6,335,029 B1 | 1/2002 | Kamath et al. | |
| 6,344,035 B1 | 2/2002 | Chudzik et al. | |
| 6,346,110 B2 | 2/2002 | Wu | |
| 6,358,556 B1 | 3/2002 | Ding et al. | |
| 6,379,381 B1 | 4/2002 | Hossainy et al. | |
| 6,387,379 B1 | 5/2002 | Goldberg et al. | |
| 6,395,326 B1 | 5/2002 | Castro et al. | |
| 6,419,692 B1 | 7/2002 | Yang et al. | |
| 6,451,373 B1 | 9/2002 | Hossainy et al. | |
| 6,475,779 B2 | 11/2002 | Mathiowitz et al. | |
| 6,482,834 B2 | 11/2002 | Spada et al. | |
| 6,494,862 B1 | 12/2002 | Ray et al. | |
| 6,503,538 B1 | 1/2003 | Chu et al. | |
| 6,503,556 B2 | 1/2003 | Harish et al. | |
| 6,503,954 B1 | 1/2003 | Bhat et al. | |
| 6,506,437 B1 | 1/2003 | Harish et al. | |
| 6,514,286 B1 | 2/2003 | Leatherbury et al. | |
| 6,524,347 B1 | 2/2003 | Myers et al. | |
| 6,527,801 B1 | 3/2003 | Dutta | |
| 6,527,863 B1 | 3/2003 | Pacetti et al. | |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | |
| 6,544,223 B1 | 4/2003 | Kokish | |
| 6,544,543 B1 | 4/2003 | Mandrusov et al. | |
| 6,544,582 B1 | 4/2003 | Yoe | |
| 6,555,157 B1 | 4/2003 | Hossainy | |
| 6,558,733 B1 | 5/2003 | Hossainy et al. | |
| 6,565,659 B1 | 5/2003 | Pacetti et al. | |
| 6,572,644 B1 | 6/2003 | Moein | |
| 6,585,755 B2 | 7/2003 | Jackson et al. | |
| 6,585,765 B1 | 7/2003 | Hossainy et al. | |
| 6,585,926 B1 | 7/2003 | Mirzaee | |
| 6,605,154 B1 | 8/2003 | Villareal | |
| 6,613,432 B2 | 9/2003 | Zamora et al. | |
| 6,616,765 B1 | 9/2003 | Hossaony et al. | |
| 6,620,617 B2 | 9/2003 | Mathiowitz et al. | |
| 6,623,448 B2 | 9/2003 | Slater | |
| 6,625,486 B2 | 9/2003 | Lundkvist et al. | |
| 6,641,611 B2 | 11/2003 | Jayaraman | |
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,689,350 B2 | 2/2004 | Uhrich | |
| 6,695,920 B1 | 2/2004 | Pacetti et al. | |
| 6,706,013 B1 | 3/2004 | Bhat et al. | |
| 6,709,514 B1 | 3/2004 | Hossainy | |
| 6,710,126 B1 | 3/2004 | Hirt et al. | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |
| 6,730,064 B2 | 5/2004 | Ragheb et al. | |
| 6,733,768 B2 | 5/2004 | Hossainy et al. | |
| 6,740,040 B1 | 5/2004 | Mandrusov et al. | |

(56) References Cited

U.S. PATENT DOCUMENTS

| | | |
|---|---|---|
| 6,743,462 B1 | 6/2004 | Pacetti |
| 6,746,773 B2 | 6/2004 | Llanos et al. |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,776,796 B2 | 8/2004 | Falotico et al. |
| 6,780,424 B2 | 8/2004 | Claude |
| 6,790,228 B2 | 9/2004 | Hossainy et al. |
| 6,824,559 B2 | 11/2004 | Michal |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,890,583 B2 | 5/2005 | Chudzik et al. |
| 6,899,731 B2 | 5/2005 | Li et al. |
| 7,008,667 B2 | 3/2006 | Chudzik et al. |
| 2001/0007083 A1 | 7/2001 | Roorda |
| 2001/0029351 A1 | 10/2001 | Falotico et al. |
| 2001/0037145 A1 | 11/2001 | Guruwaiya et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0111590 A1 | 8/2002 | Davila et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0162940 A1* | 8/2003 | Shalaby ................ 528/425 |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0106987 A1 | 6/2004 | Palasis et al. |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0113903 A1 | 5/2005 | Rosenthal et al. |
| 2005/0208093 A1* | 9/2005 | Glauser et al. ................ 424/423 |
| 2005/0220880 A1* | 10/2005 | Lewis et al. ................ 424/486 |
| 2005/0245637 A1* | 11/2005 | Hossainy et al. ............ 523/113 |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 216 717 | 6/2002 |
| EP | 1 273 314 | 1/2003 |
| EP | 1 407 786 | 3/2006 |
| JP | 2001-190687 | 7/2001 |
| JP | 2006-152306 | 6/2006 |
| JP | 2007-530733 | 11/2007 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 85/03444 | 8/1985 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/11724 | 4/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |

(56) References Cited

FOREIGN PATENT DOCUMENTS

| | | |
|---|---|---|
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2005/092406 | 10/2005 |

OTHER PUBLICATIONS

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cqi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis($\alpha$-amino acid)$\alpha$,$\omega$-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising $\alpha$-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

va Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Translation of Japanese Notice of Reasons for Rejection for appl. No. P2009-541542, dispatched Jan. 8, 2013, 4 pgs.

\* cited by examiner

COATING OF FAST ABSORPTION OR DISSOLUTION

BACKGROUND OF THE INVENTION

1. Field of the Invention

This invention generally relates to a coating of fast dissolution or absorption on an implantable device.

2. Description of the Background

Blood vessel occlusions are commonly treated by mechanically enhancing blood flow in the affected vessels, such as by employing a stent. Stents are used not only for mechanical intervention but also as vehicles for providing biological therapy. To affect a controlled delivery of an active agent in stent based therapy, the stent can be coated with a biocompatible polymeric coating. The biocompatible polymeric coating can function either as a permeable layer or a carrier to allow a controlled delivery of the agent. A continuing challenge in the art of implantable stents is to provide a coating that possesses good biobeneficial properties, which refer to good biocompatibilities in both the acute and chronic timeframes.

Generally, a polymer forming a coating composition for an implantable device has to be at least biologically benign. Additionally, the polymer could have a therapeutic effect either additively or synergistically with the bioactive agent. The polymer is preferably biocompatible. To provide for a coating that is biologically benign, various compositions have been used with limited success. For example, coating compositions containing poly(ethylene glycol) have been described (see, for example, U.S. Pat. No. 6,099,562). One of the needs in the art is to provide for a stent that has favorable long-term biological properties. However, under certain circumstances, it is documented that polymer and remaining drugs on the stents are major factors in causing late clinical effects such as late stent thrombosis, in stent artherosclerosis, and late stent malapposition.

The various embodiments described below address the above described problems.

SUMMARY OF THE INVENTION

Provided herein is a coating of fast absorption or dissolution. The coating includes a polymer or material of fast absorption or dissolution. By "fast absorption" or "fast dissolution" it is meant that the coating can quickly absorb or dissolve by degradation or solvation. For example, in some embodiments, about 50 weight percents of the coating can absorb or dissolve within about 24 hours after deployment of the implantable device. As used herein, the term absorption or dissolution is independent of location. In some embodiments, the absorption or dissolution occurs in a tissue. In some embodiments, the absorption or dissolution can occur in a blood vessel, for example, arteries or veins. In some further embodiments, the absorption or dissolution can occur in a disease site in need of treatment by the implantable device described herein. The type of fluid causing the absorption or dissolution described herein can be any body fluid. In some embodiments, the body fluid is a physiological fluid in a body tissue. In some embodiments, the body fluid is blood.

In some embodiments, the polymers or materials for forming the coating shall have a hydrophilicity that renders the polymers or materials soluble in the blood stream or have a molecular weight sufficiently low so that it can readily dissolve or degrade in the blood stream or a tissue. In some embodiments, the polymers or materials can have a weight average molecular weight ($M_w$) of about 100,000 Daltons or below, about 50,000 Daltons or below (e.g., about 45,000 Daltons), about 10,000 Daltons or below, about 5,000 Daltons or below, or about 2,000 Daltons or below (e.g., about 1,000 Daltons).

Such polymer or material can be ionic or non-ionic. In some embodiments, the polymer or material can bear a positive or negative charge(s). In some embodiments, the polymer or materials can include a polymer poly(ethylene glycol) (PEG), poly(vinyl alcohol) (PVA), hyaluronic acid, hydroxyl cellulose, CMC (carboxymethyl cellulose), hydroxy propyl methyl cellulose (HPMC), hydroxy propyl methacrylamide (HPMA), poly(butylene terephthalate-co-poly(ethylene glycol) (PBT-PEG), poly(butylene terephthalate-co-carboxy methyl cellulose) (PBT-co-CMC), polysaccaride, a phosphoryl choline polymer, chitosan, collagen, or combinations thereof.

In some embodiments, the dissolution or absorption rate can be increased by blending a small amount of low molecular weight polymer into the coating. In some embodiments, polymers with basic or acidic pendant groups can be included in a coating to increase the dissolution or absorption rate of the coating.

The thickness of the coating relates to the rate of dissolution or absorption if the dissolution or absorption of the coating is by a mechanism that includes surface erosion. In some embodiments, the coating can have various thicknesses. The coating can have a thickness ranging from about 10 nm to about 1 mm. In some embodiments, the coating can have a thickness of about 1 µm, about 3 µm, about 5 µm, about 10 µm, about 20 µm or about 50 µm. In some embodiments, the coating can have a thickness ranging from about 2 µm to about 10 µm.

In some embodiments, the coating includes a therapeutic substance. The therapeutic substance can have a release rate that is substantially the same as the absorption rate of the coating if release of the therapeutic substance is by a mechanism that includes surface erosion. In some embodiments, the therapeutic substance can have a release rate that is faster than the absorption rate of the coating.

In some embodiments, the therapeutic substance can have a release rate that is slower the absorption rate of the coating. For example, where a coating includes a layer without the therapeutic substance on top of a reservoir layer including the therapeutic substance, the release rate of the therapeutic substance can be slower than the absorption rate of the coating.

The coating described herein can be formed on an implantable device such as a drug delivery stent. The coating may optionally include one or more bioactive agents. Some examples of the bioactive agent that can be included in the coating or implantable device include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, mometasone, statins, CD-34 antibody, abciximab (REOPRO), progenitor cell capturing antibody, prohealing drugs, prodrugs thereof, co-drugs thereof, or a combination thereof.

The implantable device having the coating described herein can be used for treating, preventing, or ameliorating a medical condition such as atherosclerosis, thrombosis, restenosis, hemorrhage, vascular dissection or perforation, vascular aneurysm, vulnerable plaque, diabetes, chronic total occlusion, claudication, anastomotic proliferation (for vein and artificial grafts), bile duct obstruction, ureter obstruction, tumor obstruction, or combinations of these.

DETAILED DESCRIPTION

Figure 1:
FIG. 1 is the scanning electron microscopy (SEM) image of a coating on a stent including a phosphoryl choline polymer before simulated use. The coating has a drug/polymer ratio of 1:5.

Provided herein is a coating of fast absorption or dissolution. The coating includes a polymer or material of fast absorption or dissolution. By "fast absorption" or "fast dissolution" it is meant that the coating can quickly absorb or dissolve by degradation or solvation. For example, in some embodiments, about 50 weight percents of the coating can absorb or dissolve within about 24 hours after deployment of the implantable device. As used herein, the term absorption or dissolution is independent of location. In some embodiments, the absorption or dissolution occurs in a tissue. In some embodiments, the absorption or dissolution can occur in a blood vessel, for example, arteries or veins. In some further embodiments, the absorption or dissolution can occur in a disease site in need of treatment by the implantable device described herein. The type of fluid causing the absorption or dissolution described herein can be any body fluid. In some embodiments, the body fluid is a physiological fluid in a body tissue. In some embodiments, the body fluid is blood.

In some embodiments, the polymers or materials for forming the coating shall have a hydrophilicity that renders the polymers or materials soluble in the blood stream or have a molecular weight sufficiently low so that it can readily dissolve or degrade in the blood stream or a tissue. For example, the polymers or materials can have a weight-average molecular weight ($M_w$) ranging from about 1,000 Daltons to about 150,000 Daltons, e.g., from about 10,000 Dalton to about 150,000 Daltons or from about 50,000 Daltons to about 100,000 Daltons. In some embodiments, the polymers or materials can have a $M_w$ of about 100,000 Daltons or below, about 50,000 Daltons or below (e.g., about 45,000 Daltons), about 10,000 Daltons or below, about 5,000 Daltons or below, or about 2,000 Daltons or below (e.g., about 1,000 Daltons).

Such polymer or material can be ionic or non-ionic. In some embodiments, the polymer or material can bear a positive or negative charge(s). In some embodiments, the polymer or materials can include a polymer poly(ethylene glycol) (PEG), poly(vinyl alcohol) (PVA), hyaluronic acid, hydroxyl cellulose, CMC (carboxymethyl cellulose), hydroxy propyl methyl cellulose (HPMC), hydroxy propyl methacrylamide (HPMA), poly(butylene terephthalate-co-poly(ethylene glycol) (PBT-PEG), poly(butylene terephthalate-co-carboxy methyl cellulose) (PBT-co-CMC), polysaccharide, a phosphoryl choline polymer, chitosan, collagen, or combinations thereof.

In some embodiments, the dissolution or absorption rate can be increased by blending a small amount of low molecular weight polymer into the coating. In some embodiments, polymers with basic or acidic pendant groups can be included in a coating to increase the dissolution or absorption rate of the coating. The term "low molecular weight" generally refers to a weigh-average molecular weight ("$M_w$") below about 45,000 Daltons, e.g., below about 30,000 Daltons, below about 20,000 Daltons, below about 10,000 Daltons, below about 5,000 Daltons, or below about 1,000 Daltons. In some embodiments, the term "low molecular weight" can be in a range between about 300 and about 5,000 Daltons, e.g., between about 1,000 Daltons to about 5,000 Daltons. The term "small amount" refers to a weight percentage of about 1% to about 10%, about 1% to about 5%, or about 5% to about 10%. In some embodiments, the term "small amount" can refer to a weight percentage of below about 1%. In some embodiments, the term "small amount" can refer to a weight percentage of above 10%, e.g., about 15% or about 20%.

The thickness of the coating relates to the rate of dissolution or absorption if the dissolution or absorption of the coating is by a mechanism that includes surface erosion. In some embodiments, the coating can have various thicknesses. The coating can have a thickness ranging from about 10 nm to about 1 mm. In some embodiments, the coating can have a thickness of about 1 μm, about 3 μm, about 5 μm, about 10 μm, about 20 μm or about 50 μm. In some embodiments, the coating can have a thickness ranging from about 2 μm to about 10 μm.

In some embodiments, the coating includes a therapeutic substance. The therapeutic substance can have a release rate that is substantially the same as the absorption rate of the coating if release of the therapeutic substance is by a mechanism that includes surface erosion. In some embodiments, the therapeutic substance can have a release rate that is faster than the absorption rate of the coating.

In some embodiments, the therapeutic substance can have a release rate that is slower the absorption rate of the coating. For example, where a coating includes a layer without the therapeutic substance on top of a reservoir layer including the therapeutic substance, the release rate of the therapeutic substance can be slower than the absorption rate of the coating.

The coating described herein can be formed on an implantable device such as a drug delivery stent. The coating may optionally include one or more bioactive agents. Some examples of the bioactive agent that can be included in the coating or implantable device include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, mometasone, statins, CD-34 antibody, abciximab (REOPRO), progenitor cell capturing antibody, prohealing drugs, prodrugs thereof, co-drugs thereof, or a combination thereof.

The implantable device having the coating described herein can be used for treating, preventing, or ameliorating a medical condition such as atherosclerosis, thrombosis, restenosis, hemorrhage, vascular dissection or perforation, vascular aneurysm, vulnerable plaque, diabetes, chronic total occlusion, claudication, anastomotic proliferation (for vein and artificial grafts), bile duct obstruction, ureter obstruction, tumor obstruction, or combinations of these.

The scanning electron microscopy (SEM) image of a coating on a stent including a phosphoryl choline polymer before simulated use is shown in FIG. 1. The coating has a drug/polymer ratio of 1:5.

Coating Modulation

The absorption rate or dissolution rate of a coating can be modulated by modulating several parameters of the coating. Some of the factors are, e.g., (1) hydrophilicity of the coating (hydrophilic/hydrophobic ratio) (2) charge (pKa) or isoelectric point (polymers/proteins pH dependent solubility), (3) thickness of the coating, (4) coating morphology, or (5) ingredients of the composition forming the coating. Hydrophilicity of the coating pertains to water uptake of the coating and therefore relates to the absorption rate or dissolution rate of the coating. Generally, the more hydrophilic the coating, the more absorbable or dissolvable of the coating. Thickness of the coating is also related to the absorption or dissolution of the coating. While the relationship of the rate of absorption or dissolution of a particular coating with respect to the thickness of the coating depends on mechanism of absorption or dissolution, a thicker coating can dissolve or absorb slower than a thinner coating. Coating morphology relates to the rate of absorption or dissolution in that an amorphous coating generally dissolves or dissolves faster than a crystalline coating. Therefore, to control the rate of absorption or dissolution of a coating, one can tailor the above parameters according to a desired rate of absorption or dissolution.

In some embodiments, one can tailor the rate of dissolution or absorption of coating by blending a small amount of low molecular weight hydrophilic polymer into the coating matrix. Low molecular weight polymer can mean any hydrophilic polymers, such as poly(ethylene glycol) (PEG), vinyl alcohol polymer or copolymers (e.g., EVAL) having a molecular weight below about, e.g., 5,000 Daltons, below about 1,000 Daltons, or below about 500 Daltons. In some embodiments, the coating matrix can include a small amount unpolymerized monomer or comonomer. In some embodiments, the low molecular hydrophilic polymer can include acidic or basic end groups, etc. Such acidic groups can be, for example, carboxylic acid group, sulfonic acid group, or phosphonic acid group. Such basic groups, can be, for example, amino group or a salt of the carboxylic acid, sulfonic acid, or phosphonic acid groups.

In some embodiments, the coating can be formed to have a thickness so that renders the coating capable of fast absorption or dissolution. For example, the coating can have a thickness ranging from about 10 nm to about 1 mm. In some embodiments, the coating can have a thickness of about 1 μm, about 5 μm, about 10 μm, about 20 μm or about 50 μm. In some embodiments, the coating can have a thickness ranging from about 2 μm to about 10 μm, e.g., about 3 μm.

Phosphoryl Choline Polymers

Phosphoryl choline (PC) is a zwitterionic functionality that mimics the outer surface of a lipid bilayer. It has good hemocompatibility, non-thrombogenicity, arterial tissue acceptance and long-term in-vivo stability. It has been used to increase the biocompatibility of polymers, especially of acrylic copolymers. As used herein, the term "phosphoryl choline polymer" refers to any polymer that includes at least one phosphoryl choline moiety. The phosphoryl choline polymer can be a block copolymer or a random copolymer. The phosphoryl choline polymer can have a molecular weight or hydrodynamic volume low enough to clear from the kidneys or degrade into species or fragments of a molecular weight or hydrodynamic volume low enough to clear from the kidneys. For example, the phosphoryl choline polymer can have or degrade into species or fragments that have a molecular weight below about 45,000 Daltons, e.g., about 40,000 Daltons, about 30,000 Daltons, about 20,000 Daltons, about 10,000 Daltons, about 5,000 Daltons, or about 1,000 Daltons. As used herein, the term hydrodynamic volume refers to the volume of a polymer coil when it is in solution, which can vary for a polymer depending on how well it interacts with the solvent, and the polymer's molecular weight.

In some embodiments, the phosphoryl choline polymer can be formed by polymerizing a phosphoryl choline bearing monomer and optionally monomers without phosphoryl choline. The phosphoryl choline polymer can have different molecular weight, degree of polymerization (DP), or distributions or molar ratios of monomers that have no phosphoryl choline to monomers that bear phosphoryl choline.

In another embodiment, the biocompatible polymer useful as moiety of the copolymer comprising phosphoryl choline is a non-degradable polymer. Representative biocompatible, non-degradable polymers include, but are not limited to, ethylene vinyl alcohol copolymer (commonly known by the generic name EVOH or by the trade name EVAL), polyurethanes, silicones, polyesters, polyolefins, polyisobutylene and ethylene-alphaolefin copolymers, styrene-isobutyl-styrene triblock copolymers, acrylic polymers and copolymers, vinyl halide polymers and copolymers such as poly(vinyldifluoride-co-hexafluoropropane), poly(chlorotrifluoroethylene-co-hexafluoropropane), polyvinyl ethers such as polyvinyl methyl ether, polyvinylidene halides such as polyvinylidene fluoride and polyvinylidene chloride, polyfluoroalkenes, polyperfluoroalkenes, polyacrylonitrile, polyvinyl ketones, polyvinyl aromatics such as polystyrene, polyvinyl esters such as polyvinyl acetate, copolymers of vinyl monomers with each other and olefins, such as ethylenemethyl methacrylate copolymers, acrylonitrile-styrene copolymers, ABS resins, and ethylene-vinyl acetate copolymers, polyamides such as Nylon 66 and polycaprolactam, alkyd resins, polyoxymethylenes, polyimides, polyethers, epoxy resins, rayon, rayon-triacetate, polyurethanes, silk, silk-elasitn, polyphosphazenes and combinations thereof. In some embodiments, the phosphoryl choline polymer can specifically exclude any of the above polymers.

In a further embodiment, the copolymer described herein comprises one or more of the following hydrophobic monomers: methylmethacrylate (MMA), ethylmethacrylate (EMA), butylmethacrylate (BMA), 2-ethylhexylmethacrylate, laurylmethacrylate (LMA), or combinations thereof. By varying the copolymer's content of the hydrophobic monomers, mechanical properties such as elasticity and toughness can be modulated. For example, a monomer having a relatively long side chain would enhance the flexibility of a coating comprising the copolymer. In contrast, a monomer having a relatively short side chain would enhance the rigidity and toughness of a coating comprising the copolymer.

In a further embodiment, the copolymer described herein comprises one or more of the following hydrophilic monomers: non-fouling monomers such as hydroxylethyl methacrylate (HEMA), PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, 3-trimethylsilylpropyl methacrylate (TMSPMA), and combinations thereof. The carboxylic acid bearing monomers or hydroxyl bearing monomers can be used to crosslink the copolymer once it is applied to the substrate to coat. This will hinder a very hydrophilic coating from dissolving away.

In some embodiments, the phosphoryl choline polymer can specifically exclude any units derived from the above-identified monomer(s).

In some embodiments, the phosphoryl choline polymer can be a block copolymer. The block copolymer can be formed by coupling a biocompatible polymer and a phosphoryl choline moiety. Representative biodegradable polymers include, but are not limited to, polyesters, polyhydroxyalkanoates (PHAs), poly(ester amides) that may optionally contain alkyl, amino acid, PEG and/or alcohol groups, polycaprolactone, poly(L-lactide), poly(D,L-lactide), poly(D,L-lactide-co-PEG) block copolymers, poly(D,L-lactide-co-trimethylene carbonate), polyglycolide, poly(lactide-co-glycolide), polydioxanone (PDS), polyorthoester, polyanhydride, poly(glycolic acid-co-trimethylene carbonate), polyphosphoester, polyphosphoester urethane, poly(amino acids), polycyanoacrylates, poly(trimethylene carbonate), poly(iminocarbonate), polycarbonates, polyurethanes, copoly(ether-esters) (e.g. PEO/PLA), polyalkylene oxalates, polyphosphazenes, PHA-PEG, and combinations thereof. The PHA may include poly(α-hydroxyacids), poly(β-hydroxyacid) such as poly(3-hydroxybutyrate) (PHB), poly(3-hydroxybutyrate-co-valerate) (PHBV), poly(3-hydroxyproprionate) (PHP), poly(3-hydroxyhexanoate) (PHH), or poly(4-hydroxyacid) such as poly poly(4-hydroxybutyrate), poly(4-hydroxyvalerate), poly(4-hydroxyhexanoate), poly(hydroxyvalerate), poly(tyrosine carbonates), poly(tyrosine acrylates).

In some embodiments, the phosphoryl choline polymer can specifically exclude any of the above polymers. In some embodiments, the phosphoryl choline block copolymer comprises poly(ester amide) (PEA-PC).

Methods of Phosphoryl Choline Polymers

The copolymer described herein can be synthesized by introducing phosphoryl choline into a polymer or by introducing phosphoryl choline into a monomer to form a phosphoryl choline monomer and then polymerizing the phosphoryl choline monomer to form the phosphoryl choline polymer.

In some embodiments, the phosphoryl choline can be introduced into the polymer via a reactive functionality, which can be, for example, hydroxyl groups, amino groups, halo groups, carboxyl groups, thiol groups, aldehyde, N-hydroxysuccinimide (NHS). Alternatively, phosphoryl choline can be introduced into a monomer such as an oxirane. Polymerization of the monomers can generate a phosphoryl choline polymer.

Monomers bearing phosphoryl choline can polymerize alone or with other comonomers by means known in the art e.g., catalytic polymerization, chemical reaction, or free radical polymerization, to form respective polymers bearing phosphoryl choline moiety(ies).

In some embodiments, the phosphoryl choline polymer can be a copolymer. The copolymer can be formed of a monomer bearing no phosphoryl choline and another monomer bearing phosphoryl choline. In some embodiments, the monomer bearing no phosphoryl choline can be a vinyl monomer. An example of the phosphoryl choline polymer can be formed according to scheme I.

Scheme I

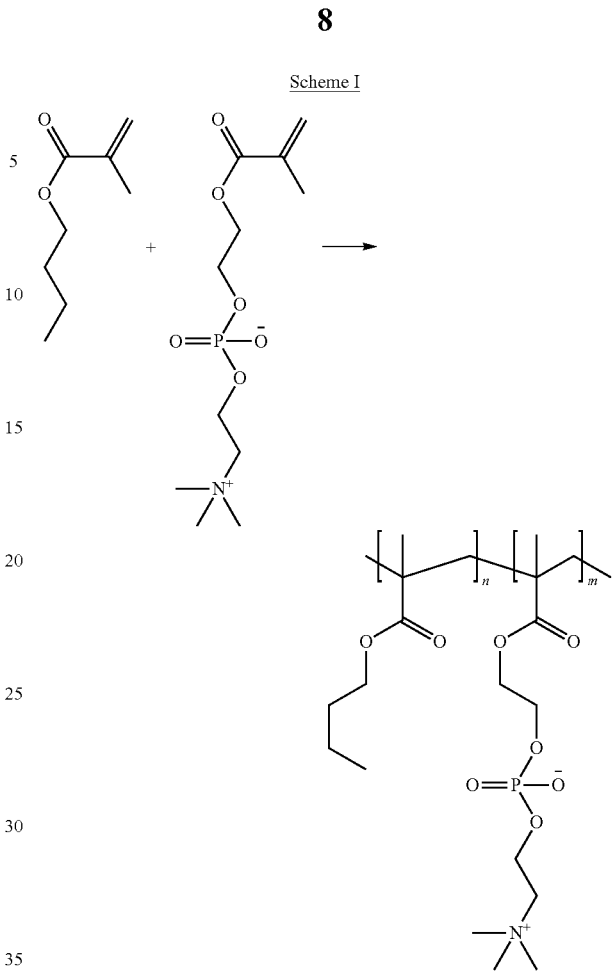

The monomers forming the phosphoryl choline polymer can have different molar percentage. Generally, the molar percentage of the monomers can independently range from 0 to 100. For example, the molar percentage of the monomers can independently be about 1, about 5, about 10, about 20, about 30, about 40, about 50, about 60, about 70, about 80, about 90, about 95, or about 99. For example, in the polymer of scheme I, n and m, which represent the molar percentages of the two monomers forming the phosphoryl choline polymer in the scheme, can be about 50 and 50. In some embodiments, n and m can be expressed as molar ratios of the monomers forming a phosphoryl choline copolymer. For example, n and m can independently range from about 0.01 to about 0.99. In some embodiments, n and m can be about 0.5.

Various methods of forming a phosphoryl choline polymer has been described in U.S. application Ser. No. 10/807,362, filed on Mar. 22, 2004, the teachings of which are incorporated herein in their entirety by reference.

Coating Construct

The coating described herein can have any suitable coating construct. For example, the polymer or material of fast absorption or dissolution can be included in the coating as a top-coat over a reservoir layer or matrix that includes a therapeutic substance. In some embodiments, the fast absorption polymer or material can form the coating alone or with another polymer. In some embodiments, the fast absorption polymer or material can include at least one therapeutic substance(s) (e.g., a drug or drugs).

In some embodiments, the coating including a polymer or material of fast absorption can have a multilayer construct. For example, the coating can have multiple layer of coating matrix. As used herein, the term "coating matrix" or "matrix coating" refers a layer of coating different from a topcoat or a primer layer of the coating.

Bioactive Agents

In some embodiments, the coating or device having the features described herein can include one or more bioactive agents. The bioactive agents can be any bioactive agent that is therapeutic, prophylactic, or diagnostic. These agents can have anti-proliferative or anti-inflammatory properties or can have other properties such as antineoplastic, antiplatelet, anti-coagulant, anti-fibrin, antithrombonic, antimitotic, antibiotic, antiallergic, and antioxidant properties. These agents can be cystostatic agents, agents that promote the healing of the endothelium such as nitric oxide releasing or generating agents, agents that attract endothelial progenitor cells, or agents that promote the attachment, migration and proliferation of endothelial cells (e.g., natriuretic peptide such as CNP, ANP or BNP peptide or an RGD or cRGD peptide), while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, mometasone, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents that may be appropriate include alpha-interferon, pimecrolimus, imatinib mesylate, midostaurin, bioactive RGD, and genetically engineered endothelial cells. The foregoing substances can also be used in the form of prodrugs or co-drugs thereof. The foregoing substances also include metabolites thereof or prodrugs of the metabolites. The foregoing substances are listed by way of example and are not meant to be limiting. Other active agents that are currently available or that may be developed in the future are equally applicable such as statins and their derivatives or analogues.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skills in the art.

Examples of Medical Devices

As used herein, a medical device may be any suitable medical substrate that can be implanted in a human or veterinary patient. Examples of such medical devices include self-expandable stents, balloon-expandable stents, stent-grafts, grafts (e.g., aortic grafts), heart valve prostheses, cerebrospinal fluid shunts, pacemaker electrodes, catheters, and endocardial leads (e.g., FINELINE and ENDOTAK, available from Guidant Corporation, Santa Clara, Calif.), anastomotic devices and connectors, orthopedic implants such as screws, spinal implants, and electro-stimulatory devices. The underlying structure of the device can be of virtually any design. The device can be made of a metallic material or an alloy such as, but not limited to, cobalt chromium alloy (EL-GILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa.

"MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable (e.g., bioabsorbable stent) or biostable polymers could also be used with the embodiments of the present invention.

Method of Use

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, radial artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

The implantable device can be implanted in any mammal, e.g., an animal or a human being. In some embodiments, the implantable device can be implanted in a patient in need of treatment by the implantable device. The treatment can be angioplasty or other type of treatments involving an implantable device.

A patient who receives the implantable device described herein can be male or female under normal body condition (e.g., normal weight) or abnormal body condition (e.g., underweight or overweight). The patient can be in any age, preferably, the patient is in an age ranging from about 40 to 70 years. An index for measuring the body condition of a patient is BMI (body mass index). A patient can have a BMI ranging from about 18 to about 30 or above.

The implantable device described herein can be used to treat or ameliorate a medical condition such as atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction, tumor obstruction, or combinations thereof.

Figure 2:
FIG. 2 is the SEM image of the coating in FIG. 1 after the simulated use.
Figure 3:
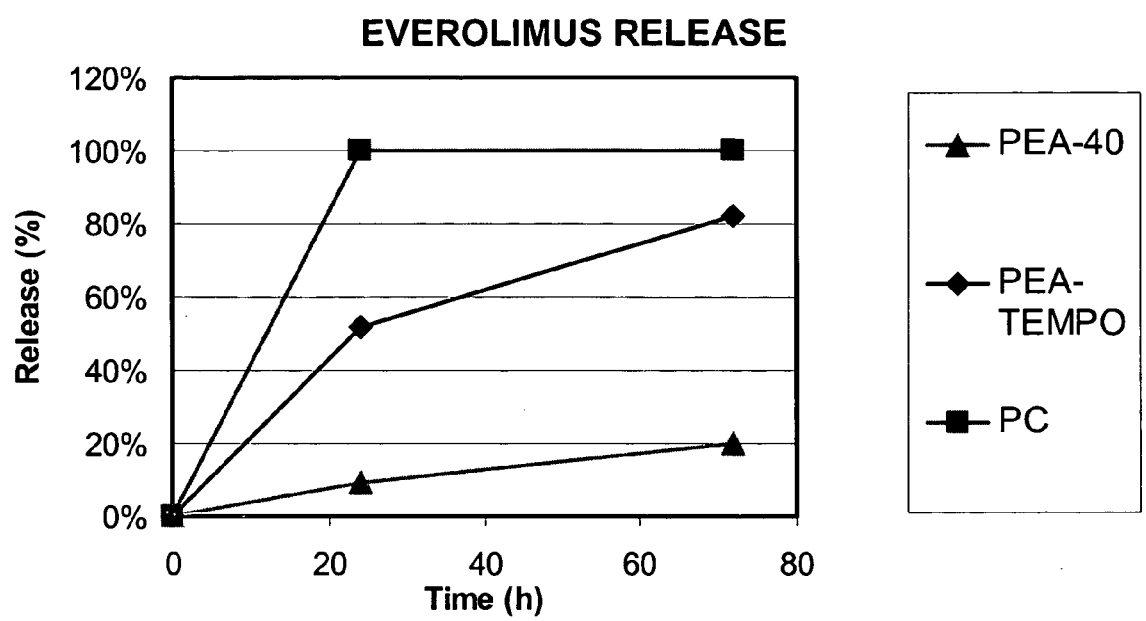
FIG. 3 shows the release rate of everolimus from a poly (ester amide) (PEA) coating, a PEA-TEMPO coating, and a coating of phosphoryl choline polymer, respectively.

FIG. 1 shows an SEM image of a drug delivery stent spray coated with a poly(phosphoryl choline-co-butyl methacrylate) (NOF, Japan) and everolimus (Novartis, Switzerland) solution at a polymer/drug ratio of 5:1. The ratio of the phosphoryl choline to butyl monomers were 50/50 and the Mw of the polymer was approximately 100,000 Daltons as measured by GPC using RI-detector. The solid concentration used for spraying were 2% using a mixture of solvents (CH2Cl2 50% (w/w), CH3OH 25% (w/w), DMAc 25% (w/w)). FIG. 2 is the SEM image of the coating in FIG. 1 after simulated use. The simulated use were performed in synthetic artery made from PVA using PBS saline buffer. The stent were tested for one hour before being removed and analyzed by SEM at which it was observed that all polymer had been removed FIG. 3 shows the release rate of everolimus from a poly(ester amide) (PEA) coating, a PEA-TEMPO coating, and a coating made of the above mentioned phosphoryl choline polymer, respectively. The total content of the various drug delivery stents were determined and used to calculate the remaining amount of drug in the coating after immersing in porcine serum for 24, and 72 h respectively. As expected the drug was completely release at 24 h for the bioabsorbable or soluble phosphoryl-choline coating.

While particular embodiments of the present invention have been shown and described, it will be obvious to those skilled in the art that changes and modifications can be made without departing from this invention in its broader aspects. Therefore, the appended claims are to encompass within their scope all such changes and modifications as they fall within the true spirit and the scope of this invention.

What is claimed is:
1. A coating on an implantable device, the coating comprising a phosphoryl choline polymer, wherein about 50 wt % or more of the coating can absorb or dissolve within 24 hours after implantation,
wherein the phosphoryl choline polymer comprises at least one phosphoryl choline moiety and at least one moiety derived from a biocompatible polymer,
wherein the biocompatible polymer comprises poly(ester amide), poly(lactic acid), poly(glycolic acid), poly(caprolactone), poly(dioxanone), or poly(ester amide-2,2,6,6-tetramethyl-1-piperidinyloxy) (PEA-TEMPO),
wherein phosphoryl choline polymer comprises a fragment having the formula of

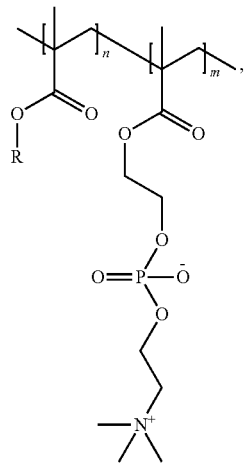

Formula X wherein R is selected from the group consisting of methyl, ethyl, propyl, and butyl group,
where n and in are the fractional percentage of monomers in phosphoryl choline polymer and independently range from about 0.01 to about 0.99, wherein the fragment of Formula X has a Mw of 10,000 Daltons or below.

2. The coating of claim 1, wherein the fragment of Formula X has a Mw of 5000 Daltons or below.

3. The coating of claim 1, wherein n and m are each about 0.5.

4. The coating of claim 1, wherein the phosphoryl choline polymer is random or block copolymer.

5. The coating of claim 1, further comprising a bioactive agent.

6. The coating of claim 5, wherein the bioactive agent is selected from the group consisting of paclitaxel, docetaxel, estradiol, nitric oxide donors, super oxide dismutases, 4 amino-2,2,6,6-tetramethyl piperidine-1-oxyl (4-amino-TEMPO), tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, mometasone, CD-34 antibody, abciximab (REOPRO), progenitor cell capturing antibody, prodrugs thereof, or a combination thereof.

7. The coating of claim 1, wherein the implantable device is a stent.

8. A method of treating a disorder in a human being by implanting in the human being an implantable device comprising the coating of claim 1, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

* * * * *